United States Patent [19]

Sherman et al.

[11] 4,310,510

[45] Jan. 12, 1982

[54] SELF ADMINISTRABLE ANTI-FERTILITY COMPOSITION

[76] Inventors: Kenneth N. Sherman, 135 Heather La., Wilton, Conn. 06897; Arnold Jacobson, 53 E. Altarinda Dr., Orinda, Calif. 94563

[21] Appl. No.: 193,628

[22] Filed: Oct. 3, 1980

Related U.S. Application Data

[60] Division of Ser. No. 754,737, Dec. 27, 1976, Pat. No. 4,252,787, which is a continuation-in-part of Ser. No. 642,797, Dec. 22, 1975, abandoned, which is a continuation-in-part of Ser. No. 430,645, Jan. 4, 1974, abandoned, which is a continuation-in-part of Ser. No. 225,591, Feb. 11, 1972, abandoned.

[51] Int. Cl.$^3$ .................... A61K 9/02; A61K 9/12
[52] U.S. Cl. .................... 424/45; 424/238; 424/211; 424/212; 424/243
[58] Field of Search ............ 424/238–243, 424/45

[56] References Cited

U.S. PATENT DOCUMENTS

| | | | |
|---|---|---|---|
| 2,943,979 | 7/1960 | Elias | 424/16 |
| 3,170,464 | 2/1965 | Forti et al. | 128/271 |
| 3,219,525 | 11/1965 | Berkow et al. | 424/45 |
| 3,244,589 | 4/1966 | Sunnen et al. | 424/45 |
| 3,262,450 | 7/1966 | Elias | 128/270 |
| 3,342,181 | 9/1967 | Jacquignon | 128/260 |
| 3,384,541 | 5/1968 | Clark | 424/45 |
| 3,443,563 | 5/1969 | Ishihama et al. | 128/271 |
| 3,545,439 | 12/1970 | Duncan | 128/260 |
| 3,572,335 | 3/1971 | Robinson | 128/6 |

FOREIGN PATENT DOCUMENTS

177/65 of 0000 Ireland.

OTHER PUBLICATIONS

Ringler, Steriods, 7(4): 341–349, Apr. 1966, "Efficacy of Topically Applied Progestational Agents".
Shipley, Steroids 5(5): 699–717, May 1965, "Effectiveness of Topical Application of a Number of Progestins".
Kincl et al., Steroids 8(1): 5–11, Jul. 1966, "Inhibition of Ovulation in the Adult Estrus Rabbit by Vaginal Deposition".
Greenblatt, J. Clinical Endocrin., 14: 1564–1567, Dec. 1954, "The Physiological Effectiveness of Progesterone Vaginal Suppositories".
Cohen et al., Fertility and Sterility, Vo. 21(10), Oct. 1970, "The Effects of an Intracervical Steroid-Releasing Device on the Cervical Mucus".
Rudel et al., Birth Control: Contraception and Abortion, MacMillan Company, New York.
Schumacher, Fertility and Sterility, vol. 21(10), Oct. 1970, "Bio-Chemistry of Cervical Mucus".

*Primary Examiner*—Shep K. Rose
*Attorney, Agent, or Firm*—Sherman & Shalloway

[57] ABSTRACT

A self-administrable anti-fertility composition comprising a progestational compound in an amount effective for alteration of cervical mucus secretions in a manner unfavorable to fertility without systemic absorption and a pharmaceutically acceptable vehicle. A typical composition is a foamable aqueous emulsion containing an anionic surfactant, propylene glycol and an amount of progesterone effective to provide a dose of from about 10 micrograms to about 5 milligrams. The composition may be foamed by dispensing with a syringe or by dispensing from an aerosol container.

16 Claims, No Drawings

4,310,510

SELF ADMINISTRABLE ANTI-FERTILITY COMPOSITION

RELATED APPLICATIONS

This application is a division of application Ser. No. 754,737, filed Dec. 27, 1976, now U.S. Pat. No. 4,252,787, issued Feb. 24, 1981, which is a continuation-in-part of application Ser. No. 642,797, filed Dec. 22, 1975, now abandoned, which is a continuation-in-part of application Ser. No. 430,645, filed Jan. 4, 1974, now abandoned, which is a continuation-in-part of application Ser. No. 225,591, filed Feb. 11, 1972, now abandoned.

BACKGROUND OF THE INVENTION

This invention relates to compositions for inhibiting the fertility of female mammals wherein the fertility is initiated and characterized by deposit of semen in the vaginal cavity with subsequent transport into the genital tract. While the invention is applicable to all female mammals having this fertility characteristic, it has particular application to inhibiting the fertility of a human female.

The science of fertility inhibition and control has advanced rapidly in recent years such that the clinical efficacy of certain pharmaceutical products has become well established. In addition to orally administered products, containing one or more hormonal substances such as progestational substances and/or estrogenic substances and mechanical devices, there has recently been developed "slow release" methods of administering such products, as by the implantation in the uterine cavity of a plastic capsule containing the fertility control substance. U.S. Pat. Nos. 3,545,439 to Duncan and 3,572,335 to Robinson; Cohen, et al., "The Effects of An Intracervical Steroid-Releasing Device on the Cervical Mucus", Fertility and Sterility, Volume 21, No. 10, October 1970. A general review of the state-of-the-art of fertility control is given in Birth Control Contraception and Abortion, by Rudel, et al., The MacMillan Company, New York.

The methods of fertility inhibition to date, however, are based upon the systemic absorption of the fertility control agent, requiring large single doses or large cumulative amounts of the agent. This often results in adverse side effects. For example, it has been reported that anti-fertility preparations containing estrogen are significantly related to the occurrence of certain thromboembolic diseases such as blood clotting. Such anti-fertility preparations have also been linked to diabetes and cancer, as well as to relatively minor, but bothersome, side effects such as nausea, weight gain and nervousness. Even in those developments in which estrogenic hormones have been totally eliminated from the preparations, the mode of application is systemic, as by oral administration, which still results in more or less serious side effects both known and unknown.

A high level of efficacy in conjunction with low cost and elimination of injurious or seriously discomforting side effects are the primary requisites in an anti-fertility preparation or fertility control method. However, the development of a new fertility control product requires complex and long-term clinical trials for Government approval before the efficacy and side effects are adjudged acceptable for public use. Accordingly, a fertility-control composition and method which would minimize governmentally-required clinical trials and the like, while satisfying the other requisites, could quickly be made publicly available.

It has also been reported that certain fertility control preparations, known for their efficacy by oral administration or by surgical implantation into the uterine cavity, have some local effect on the cervical musus secretions. In particular, it is known that certain estrogenic substances cause cervical secretions which are profuse, watery, clear, alkaline and favorable for sperm penetration, and that the administration of certain progestational agents result in cervical secretions which are reduced in volume, are scanty, fixed, opaque, less alkaline or acid, contain an increased number of leukocytes, and are unfavorable for sperm penetration. The former condition of the cervical secretions are also associated with the preovulatory phase of the menstrual cycle when estrogen hormone production is at a relatively high rate, while the latter condition of the cervical secretions are associated with the postovulatory phase when production of the progesterone hormone is at a relatively high rate. In a normal or average 28-day menstrual cycle, estrogen secretion from a single follicle generally begins on the fifth day of the cycle with the beginning of the ripening of an egg in the follicle in an ovary. Progesterone production generally begins on the fourteenth day when the ripened egg bursts from the ovary to begin its 6½ day trip down the Fallopian tube to the uterus. It is also known from Schumacher, "Bio-Chemistry of Cervical Mucus", Fertility and Sterility, Volume 21, No. 10, October 1970. pp 697–705 that cervical mucus secretions having the latter characteristics represent a mechanical and bio-chemical barrier against introducing organisms such as sperms, the sperms negotiating the cervical mucus barrier only when the viscosity and other characteristics of the mucus have been sufficiently reduced. The changes in cervical mucus characteristics during a normal 28-day menstrual cycle are shown schematically in FIG. 3.13 on page 120 of the Rudel, et al. text mentioned above.

Rudel, et al. also show, at pages 104–105 (FIG. 3.8) that, at low dosage, progestogen can be taken to suppress fertility without inhibiting either endometrial development or ovulation. However, to be statistically effective in preventing fertilization in the typical female, the effective progestogen dosage is that which will suppress ovulation and endometrial development in a substantial proportion of the female population.

It is also reported by Rudel, et al. at page 106 that the progestational and antiovulatory activity of different progestogens does not always follow the same order of activity. Thus, for certain progestogens, such as norethindrone and norethindrone acetate, the effective dose for inhibiting ovulation is significantly less than the dose which will produce endometrial secretory response and generally somewhat less than the dose which will produce a thermogenic, i.e., hypothalmic effect. On the other hand, for chlormadinone acetate, the ovulation inhibitory dose is generally higher than the dose for producing secretory effects. The effective dose in mg needed to produce several progestation effects in the human is shown in the following table:

| Compound | Secretory Effects | Thermogenic Effects (Hypothalamic) | Ovulation Inhibition |
|---|---|---|---|
| Norethindrone | 10 | 0.5 | 0.4–0.5 |
| Norethindrone | | | |

-continued

| Compound | Secretory Effects | Thermogenic Effects (Hypothalamic) | Ovulation Inhibition |
|---|---|---|---|
| acetate | 5–10 | 2–4* | 2.5* |
| Chlormadinone acetate | 1–2 | 4 | 2–4 |

*Data not available for lower doses
(Taken from Rudel, et al., Table 3.4 at p. 106)

The daily dose of various progestogens needed to hihibit ovulation in women (dosing from cycle days 5 to 24) is shown in the following table:

| Compound | Inhibitory Dose (mg) | Assay Used |
|---|---|---|
| Chlormadinone acetate | 2–4 | Fertility; urinary pregnanediol and estrogens |
| Ethynodiol diacetate | 2 | LH determination |
| Lynestrol | 5 | LH determination; urinary pregnanediol |
| Norgestrel | 0.5 | LH determination; urinary pregnanediol |
| Norethindrone | 0.4 | Fertility; LH and progesterone in plasma; urinary pregnanediol and estrogens |
| Norethindrone acetate | 2 or less | Total gonadotropins and pregnanediol in urine |
| Norethynodrel | 2.5 | Pregnanediol excretion |

(Taken from Rudel, et al., Table 3.5 at p. 107)

Rudel, et al. also report on specific studies on the progestational compounds chlormadinone acetate and norethindrone with respect to cervical mucus. These results which are reported in Table 3.12 at page 121 and Table 3.13 at page 122 are reproduced below.

| No. of Patients | Daily Dose (mg) | Amount | | Transparency | | Viscosity | | Spinnbarkheit | | Ferning | |
|---|---|---|---|---|---|---|---|---|---|---|---|
| | | Normal | Decrease | Transparent | Opaque | Normal | Increase | Normal | Decrease | Normal | Decrease |
| 10 | 0.05 | 3 | 7 | 5 | 5 | 5 | 5 | 8 | 2 | 7 | 3 |
| 6 | 0.1 | 2 | 4 | 4 | 2 | 2 | 2 | 3 | 3 | 3 | 3 |
| 9 | 0.2 | 1 | 8 | 3 | 6 | 2 | 7 | 3 | 6 | 4 | 5 |
| 10 | 0.3 | 0 | 10 | 1 | 9 | 2 | 8 | 3 | 7 | 4 | 6 |
| 10 | 0.4 | 0 | 10 | 0 | 10 | 0 | 10 | 0 | 10 | 3 | 7 |
| 10 | 0.5 | 0 | 10 | 0 | 10 | 0 | 10 | 0 | 10 | 2 | 8 |

From Martinex-Manautou, J.; Giner-Velazquez, J.; and Rudel, H. W.;
"Continuous progestogen contraception: A dose relationship study with chlormadinone acetate", Fertility and Sterility, 18:57–62, 1967.

| Dose (mg) | No. of Patients | Neg. | Percentage Response | | | |
|---|---|---|---|---|---|---|
| | | | Poor | Reg. | Good | Excellent |
| 0.1 | 23 | 0.0 | 43.4 | 21.8 | 21.8 | 13.0 |
| 0.5 | 115 | 13.1 | 67.0 | 14.8 | 5.1 | 0.0 |

Samples of cervical mucus taken between days 9 and 16 of menstrual cycle and examined for spermatozoal motility.

Kincl, et. al. *Steroids*, 8(1): 5–11, July, 1966, "Inhibition of Ovulation in the Adult Estrus Rabbit by Vaginal Deposition", show the administration by intravaginal deposition of progestational compounds to achieve an anti-ovulatory activity. It is very clear that systemic absorption is intended and obtained and that without systemic absorption, the effect described by Kincl, et al. would not take place.

Greenblatt, J., *Clin. Endocrin.*, 14: 1564–1567, December, 1954, "The Physiological Effectiveness of Progesterone Vaginal Suppositories", describes progesterone administered in the form of vaginal suppositories; the progesterone is absorbed and is clinically effective to produce systemic effects. The point of the Greenblatt disclosure is to show how systemic absorption is as effective as oral administration in obtaining such systemic effects to provide an anti-fertility result. Clearly, Greenblatt never contemplated a topical application which would provide a non-systemic effect only.

Ringler, *Steroids*, 7(4): 341–349, April, 1966, "Efficacy of Topically Applied Progestational Agents", and Shipley, *Steroids*, 5(5): 699–717, May, 1965, "Effectiveness of Topical Application of a Number of Progestins", are similar in that both show the use of progestational steroids which are absorbed after topical application to rabbits to obtain a systemically generated anti-fertility effect. Again, systemic rather than non-systemic results are desired and obtained and in this case the topical application is only carried out as a means of applying the agent systemically. Non-systemic effects producing anti-fertility results were not contemplated by Ringler or Shipley.

Irish Pat. No. 1173/65 is similar in that it shows the topical application of a progestational agent carried in a suitable carrier such as a foam to achieve an anti-fertility effect. However, once again, the effect produced is systemic and is intended to be systemic. The reference does not suggest a non-systemic effect without, also, a systemic effect.

Nevertheless, so far as is known, there have been no known techniques for providing effective contact of the progestational compound with the cervical tissues in a self-administrable form while avoiding undesirable side effects of fertility inhibition, due principally to systemic absorption of the active ingredient.

OBJECTS AND SUMMARY

Accordingly, an object of the invention is to provide a new and improved composition of inhibiting the fertility of a female mammal by the local use of a progestational compound, but without apparent side effects resulting from systemic absorption.

Another object of the invention is to provide a new and improved composition for locally inhibiting fertility in female mammals, including female humans, which avoids the side effects of systemic absorption by oral administration and also the inconvenience and discomforture of bulky mechanical fertility control devices or slow release devices requiring surgical implantation.

An additional object is to provide a new and improved fertility control composition based in part on known and Government-approved parmaceutical preparations, thereby substantially reducing the need for clinical trials with the attendant expense and delay.

Still another object is to provide a new and improved fertility control composition which is self-administrable, independent of the time of coitus, and, therefore, less subject to loss of efficacy due to failure of application, as is often the case when fertility control is based on administration by others or upon a short term topical preparation such as a spermicide which is applied as a foam, cream, gel, or the like.

These, and other objects, features, and advantages of the invention, will be apparent from the description which follows.

In summary outline, the foregoing objects are achieved by providing a composition comprising a progestational compound in an amount effective for alteration of cervical mucus secretions in a manner unfavorable to fertility without systemic absorption and a pharmaceutically acceptable vehicle therefore, for topically contacting the cervical tissues of a female mammal, the fertility of which results from deposit of semen in the vagina.

The invention is based upon the discovery that by careful selection of the anti-fertility composition and by careful selection of dose, the progestational compound will act effectively upon the glands which produce the cervical mucus, and/or act upon the cervical mucus itself, so as to modify the cervical mucus to form a barrier to transport of sperm for contact with the ovum, but without being absorbed by the system to any substantial extent.

The term "systemic absorption" as used herein, with respect to the cervix, refers to absorption into the user in biologically statistically significant quantities, i.e., quantities sufficient to have a noticeable and measurable material effect, as determined by standard physiological tests, on another biological function or condition of the user other than the vagina, cervix or uterus and such that the blood level of the progestational compound is significantly in excess of what it is naturally.

DETAILED DESCRIPTION

The essential pharmaceutically active ingredient of the composition of the invention is a progestational compound. A great variety of such compounds are known and many are commercially available. Generally, they are steroidal and/or hormonal compounds having activity characterized by inhibition of ovulation resulting from gonadotropin suppression, and by changing in the cervical mucus and endometrium.

The term "progestational compound", as employed herein, includes not only compounds having progestational activity and no other significant level of physiological and parmacalogical activity, but also compounds which exhibit, along with progestational effects, other effects such as estrogenic, androgenic or anabolic activity, including one or more of the foregoing activities. There is no one biological assay which adequately characterizes a compound as being progestational, or progestational together with one or more other activities, since each test is modified to some extent by the estrogenic and androgenic potencies of the material undergoing the tests, and some assays are influenced differently than are others. Nevertheless, the invention may be practiced with any and all of such compounds which are capable of altering the cervical mucus secretions in a manner unfavorable to fertility, since the degree of such activity is merely a matter of routine selection among the numerous and varied compounds available.

Generally, selection of a progestational compound is based upon two principles: the efficacy of the compound in altering the cervical mucus secretions in a manner unfavorable to fertility, and activity of the compound in dosages which are not systemically absorbed to a substantial extent. The latter condition is significant as it limits the compounds to those which will not give rise to the adverse side effects usually resulting from systemic use and absorption. The compounds having the foregoing properties may be used singly or in admixture in accordance with the foregoing principles of selection.

Typical of useful progestational compounds are the progestin compounds, even though certain progestins have inherent estrogenic or androgenic effects. Among the progestins may be mentioned progesterone (natural and synthetic), ethisterone, medroxyprogesterone acetate, hydroxyprogesterone caproate, norethindrone, norethynodrel, ethynodiol diacetate, dydrogesterone, dimethisterone, ethinylestrenol, chlormadinone acetate, norgestrel, cyproterone acetate, and the like. The foregoing, and numerous other progestational compounds useful, according to the invention, are listed and discussed in Goodman and Gilman, *The Pharmacalogical Basis of Therapeutics*, 3rd Ed., Chapter 69, The MacMillan Co., New York (1970). Particularly preferred compounds for practice of the invention are natural and synthetic progesterone, chlormadinone acetate, medroxyprogesterone acetate, norgestrel, and cyproterone acetate. Natural and synthetic progesterone are particularly useful since they resist systemic absorption to a greater extent than to derivatives of progesterone.

The vehicle for effective contact between the progestational compound and the cervical tissues is a pharmaceutically acceptable carrier.

Suitable carriers are of the non-solid or non-rigid type, such as viscous gels and creams, foams, effervescent type suppositories and the like which have sufficient structural stability or are viscous enough to keep the progestational compound in effective contact with the cervical tissue for sufficient time to bring about the desired modification of the cervical mucus secretions when formulated for self-administerable use.

When utilizing gels or creams, care should be taken that the carrier is not too viscous, thus making administration difficult and the contact time required between the reactive progestational ingredient and the cervical tissue overly long for the effective dose to be administered. On the other hand, liquid carriers and ordinary suppositories are undesirable in the present compositions since they have a propensity to flow and run out of the vagina. Ampoules or capsules, such as are employed in the methods of U.S. Pat. Nos. 3,545,439 and 3,572,335 are examples of solid or rigid type carriers which are excluded from the compositions of this invention.

Accordingly, any non-rigid pharmaceutically acceptable carrier may be employed which will provide the direct, topical contact of the active progestational ingredient with the cervical tissues and a local, rather than absorptive, systemic effect. The active ingredient may be dissolved, dispersed or suspended in the carrier to form solutions, emulsions, suspensions, syrups or elixirs having the foregoing viscosity and structural stability requirements.

The compositions are formulated so that unlike the freely flowing liquid vehicles, the compositions will generally conform to the shape of the vaginal cavity and will not flow out of the vagina with resultant discomforture, inconvenience and possible lack of sufficiently prolonged contact with the cervical tissues. Still further, when a foam base, meaning a liquid composition which will foam when agitated, is utilized as the pharmaceutically effective carrier, it can be formulated so that the foam will collapse after a predetermined duration and so that non-pharmaceutical components can be absorbed by the system without harmful side effects.

The term "foam" is used herein in a general sense to mean a mass of bubbles resulting from agitation of the composition containing the progestational compound and the foam base. The degree of stability of the resulting foam is not critical provided the foam remains long enough for contact of the progestational compound distributed throughout the film defining the foam bubbles with the cervical tissues. The term "foam" therefore includes relatively unstable aerated masses as well as the more stable variety sometimes described as "lathers". However, the preferred compositions of the invention contain foam stabilizers in order to prolong the life of the foam and, therefore, to assure effective contact of the progestational compound with the cervical tissues.

The foam base or other carrier and total composition must be pharmaceutically acceptable, that is, all ingredients must be selected so that in admixture and in the required amounts, they will be essentially non-toxic to the cervical tissues including the vagina. In some instances, an ingredient of the composition, if used alone with the progestational compound, could be irritating to the cervical tissues. However, it is well recognized that such irritation can be avoided by other ingredients, such as emollients.

The foam base, together with the progestational compound, may be true solution, an emulsion (water-in-oil but preferably oil-in-water) or a colloidal mixture. Accordingly, the compositions may be single or multi-phase liquid systems, provided the composition will foam when agitated so that the progestational compound will be uniformly dispersed throughout the film comprising the walls of the bubbles, so as to bring the compound into good contact with the cervical tissues. The foam thus not only guarantees that the progestational compound will contact the cervical tissues but, also, because of the extremely high surface area of the foam bubbles, the dose of the progestational compound can be minimized and controlled so as to maintain the dosage below amounts which will be systemic.

Foams have been found to be highly effective in their ability to reliably apply, by self-administration, progestational compounds in non-systemic doses and, in addition, are presently widely, commercially available in many different formulations for vaginal applications. Consequently, foams have been found to be extremely important as the vehicle to obtain the benefits of the invention and provide a reliable and self-administrable system for applying progesterone in non-systemic doses and are the most preferred vehicles for applying the active ingredient in this invention.

While the essential ingredients of the compositions of the invention are the progestational compound and pharmaceutically acceptable vehicle, preferably, a foam base which contains a foaming agent, the compositions may be formulated with other pharmaceutically acceptable ingredients. For example, if the progestational compound is water insoluble, such as natural or synthetic progesterone, it will usually be first dissolved in an alcohol such as ethyl alcohol before admixture with the carrier.

The compositions may be non-aqueous although aqueous systems are preferred. For example, the progestational compound may be admixed with an ethoxylated tallow alcohol and an equal volume of a glycol such as propylene glycol, such as disclosed in U.S. Pat. No. 3,384,541. The resulting composition will foam when agitated, as by dispensing from an aerosol container or by the use of a syringe. Although the ethoxylated tallow alcohol is itself a spermicide, the anti-fertility efficacy of the composition, as a result of alteration of cervical mucus secretions, is not effected.

Suitable foaming agents may be anionic, cationic, non-ionic or amphoteric surfactants, the choice thereof depending upon a variety of factors such as compatability with the progestational compound, foaming ease, and compatability with other ingredients in the composition such as solvents, thickeners, foam stabilizers, foam builders, emollients, preservatives, buffers, emulsifiers and perfume.

Among the suitable non-ionic surfactants may be mentioned ethoxylated fatty acid or alcohols such as ethoxylated lanolin alcohols, ethoxylated alkyl phenols and the ethoxylated sorbitol esters, for example, polyoxyethylene sorbitan monolaurate. Among the suitable anionic foam forming surfactants may be mentioned lauryl sulfates of different cations, such as triethanolamine lauryl sulfate, sodium lauryl sulfate, ammonium lauryl sulfate and nonoethanolamine lauryl sulfate, and analogous cations of lauryl ether sulfate. The cationic surfactants include quaternaries such as N-lauroyl colamino formyl methyl pyridinium chloride. The amphoteric foaming surfactants include carboxylic acid adducts of imidazolinium compounds such as the "Miranol" surfactants, and N-coco betaamino propionate. The foregoing, and a host of other foaming surfactants, are listed in "Detergents and Emulsifiers", John W. McCutcheon, Inc., 1964, and in U.S. Pat. Nos. 2,467,884, 2,943,979, 2,219,525, 3,144,386, 3,325,366, 3,244,589, 3,262,450 and 3,384,541. These patents, as well as several others, such as U.S. Pat. Nos. 3,162,576, 3,178,345 and 3,272,710 disclose suitable aerosol-type foam carriers. Several of the foregoing patents also disclose specific carrier formulations, other than foams, such as gels and creams, which are suitable for the preparation and method of the invention when the proper dosage of active ingredient is present and the formulation is neither freely flowing or too viscous.

The formulations may also contain buffering agents such as phosphates, citrates or tartrates so as to maintain a pH in the range normal in the female genital tract, of the order of about 4.5 to about 7, since the normal pH of the vagina is about 4.5 and that of the cervix about 7. A substantially neutral pH is preferred. If desired, the pH may be varied by addition of an acidic material, such as citric acid, or an alkali, such as triethanolamine. The formulation may also contain preservatives such as methyl and propyl parabens (the methyl and propyl esters of p-hydroxy-benzoic acid), potassium sorbate, benzyl alcohol, and the like. However, in a preferred embodiment of the invention, the composition contains 10-50% by weight of a lower glycol such as ethylene glycol or propylene glycol as foam stabilizers. In such concentration range, the glycols prevent microbial growth and, therefore, preservatives are not required. The formulations may also contain other foam stabilizers in place of the glycols such as glycerol and the polyalkylene glycols, such as polypropylene glycol, and polyglycerols. The glycol ethers should be avoided in large amounts since their increased solvent properties tend to cause irritation of the cervical tissues.

The compositions may contain emollients such as various oils, waxes and fats but such additives normally should be present only in minor amounts as they tend to impede the ready foamability of the dispersions. Other additives include foam builders, such as the fatty acid-mono and dialkanolamides commercially available as the "Super Amides", and the aliphatic, straight chain, monohydroxy alcohols containing 14 to 22 carbon atoms, such as cetyl alcohol, myristyl alcohol and stearyl alcohol, and the various isomeric mixtures of the foregoing. Still further, the dispersions may contain thickening agents such as methyl cellulose, carboxy methyl cellulose, hydroxyethyl cellulose, hydroxypropyl cellulose, and other so-called cellulose "gums". Perfumes or fragrances also may be added, such as lavender, lemon, gardenia, and the like.

The ingredients in the compositions other than inert carriers such as water, alcohol and the glycols (which may be present in amounts of about 10–70%) generally are useful in minor proportions. For example, the foam builders are useful in a range of about 1–5% by weight, the thickeners in amount of about 0.1–2% by weight, and emollients in amounts of about 1–5% by weight. Greater amounts may be used if desired.

The preferred compositions of the invention are aqueous (oil-in-water) emulsions wherein the progestational compound is natural or synthetic progesterone, present in an amount effective to provide a dose of from about 10 micrograms to about 5 milligrams, and the foaming agent is an anionic surfactant present in an amount of about 5–20% by weight, the balance being water and additives for special properties. The preferred additives are about 20–50% by weight of ethylene glycol, propylene glycol or glycerol for foam stabilization, about 1–5% by weight of cetyl alcohol as a thickener and foam builder, about 0.1–2% by weight of hydroxyethyl cellulose or hydroxypropyl cellulose to stabilize the emulsion and the pearly white color imparted by the cetyl alcohol, and about 1–5% by weight of a coco or oleic acid-diethanolamine condensate as a foam builder and also to reduce irritation sometimes caused by the anionic surfactant.

The compositions of the invention may be formulated in known ways, for example, by first dissolving the progestational compound in a solvent and then adding the resulting solution to a mixture of one or more of the other ingredients. If a perfume is added, it is normally added into an alcohol solution with the progestational compound. Since progesterone and the long chain aliphatic alcohols in the foam base formulations are normally water insoluble, a foaming surfactant is selected which will also emulsify the long chain alcohol and the progesterone with the other ingredients, although emulsifiers may be stabilized specifically for this property.

The foaming of the dispersion when a foam base is utilized may be induced in any suitable manner, such as by shaking the dispersion. However, for convenience and self-administration, the dispersion may be charged to a pressure vessel with a propellant, the actuation of the pressure relief valve then providing the required agitation for foaming of the mixture. Any of the pharmaceutically acceptable or food-type propellants may be utilized for such purposes, such as trichlorofluoromethane, dichlorodifluoromethane, 1,2-dichloro-1,1,2,2-tetrafluoroethane and the like. Preferred propellants are the chlorofluoro alkanes or blends thereof having vapor pressures at 70° F. between 25 psig and 30 psig.

Aside from vapor pressure of the propellants, the propellants, of course, are chosen for their inertness to the formulation and non-toxicity to the cervical tissues. The "Freon" type propellants possess such characteristics. One such useful propellant mixture is 20% by weight of Freon 12 and 80% by weight of Freon 114. Other propellants include Freon C115 and Freon C318.

The propellants can be used in amounts ranging from about 5% to about 95% by volume of the total emulsion. When low concentrations are used, the foams tend to be soft, wet and collapsible and when high concentrations are used, dry stiff puffs of foam are ejected from the pressure vessel in a sputtering fashion. Consequently, a preferred preparation contains from about 5% to 15% by volume of propellant since this concentration produces a stable, long-lasting, easily metered and directed foam.

The required agitation for the foaming as well as another convenient mode of dispensing the foams is the combination of a plastic or glass vessel containing the composition and a metered cylinder with plunger or syringe by means of which the composition may be drawn up while foaming and then discharged into the vagina. By correlating the concentration of progestational compound in the composition with the capacity of the syringe, non-systemic, but effective, doses of the foam may be dispensed. Disposable, preloaded, single dosage tampon-type cartridge syringe applicators are also very convenient for the invention method.

The method of the invention is applicable to any female mammal where fertility characteristically results from deposit of semen in the vagina, since it is at this location that a barrier must be formed to prevent passage of the semen into the cervix for fertilization of the ovum. Not all mammalian species provide this environment and therefore the alteration of the cervical mucus secretions in a manner unfavorable to fertility, in order to provide a barrier to the transport of semen therethrough, is relevant only in such species. The female mammalian species typical of this class are the primates, the sub-primates, the ruminants and other mammals such as dogs, rabbits, cats, and horses. The invention has particular value for inhibition of fertility in female humans.

In this connection, the expression "alteration of cervical mucus secretions in a manner unfavorable to fertility" for the purposes of this specification means the modification of the mucal secretions in the region of the vagina and/or the regulation of the cervical glands to secrete mucus of sufficient viscosity and other characteristics, such that semen cannot effectively penetrate to the ovum and initiate normal embryonic development.

While the progestational compound and its dosage must be such as to alter the cervical mucus secretions in a manner unfavorable to fertility, it must also be substantially non-systemic. In the case of the known progestational compounds when applied to female mammals, such amounts may range from daily dosages of about 10 micrograms to about 5 milligrams, and preferably, the dosages are maintained below 0.5 milligrams daily. Amounts of other progestational compounds may differ according to the level of activity and systemic absorption characteristic of such compounds for the particular female mammal being treated, and such compounds are readily selectable on this basis. In general, systemic effects are determined by the circulating blood levels of the active ingredient, rather than merely the amount absorbed. Therefore, for any particular patient, non-systemic dosages can be determined on the basis of the known level of activity and systemic absorption characteristics as well as the individual's body weight and general body chemistry.

Although applicants do not wish to be limited to any particular theory of the effectiveness of the compositions and method of the invention, it appears that the minimal dose needed to inhibit ovulation when taken systemically would not be effective in inhibiting ovulation when topically applied to the vagina since vaginal absorption would be much less than from the stomach.

Progestogens have several effects on the body. Each is dose dependent and demonstrable only in specific tissues. Progestogens in appropriate systemic concentrations inhibit the production of cervical mucus customarily caused by estrogens. Likewise, acting on the hypothalmus, progestogens inhibit secretions of hypothalamic releasing hormones. This, in turn, results in diminished output of pituitary gonadotropins which are, therefore, insufficient to induce ovulation. Thus, ovulation is inhibited by a primary effect upon the hypothalmus. When the progestogens are introduced into the vagina, systemic absorption is minimal relative to the vaginal concentration, therefore, the effects on the hypothalmus are likewise minimal. However, because the cervix is essentially bathed in the vaginal pool of progestogen, progesterone is absorbed through the cervical epithelium and is effective directly on the endocervical glands. Thus, far higher concentrations are found in these tissues with vaginal application than is found in the hypothalmus, and thus there is an inhibition of cervical mucus secretion, but insufficient systemic concentrations to affect inhibitions of ovulation by any effect upon the hypothalmus.

The progesterone from silastic capsules exerts its major effect on the endometrium because of the proximity of the endometrium and the high concentration of progesterone found there. It effects the cervical mucus to a lesser extent because it is not as close as it is to the endometrium. For similar reasons, it does not effect the hypothalmus at all. However, a similar silastic implant placed into the hypothalmus would presumably inhibit ovulation without any effects on other organs. The present method is believed to be effective because the progesterone is immediately in contact with the endocervical glands and will inhibit cervical mucus production and characteristics and thereby prevent conception without unfavorable systemic absorption.

The compositions of the invention are applied to the cervical tissues principally in the tip of the vaginal cavity so as to provide the requisite dosage of the particular composition. A single daily application independent of the time of coitus, begining with the onset of menses and continuing throughout the menstrual cycle, is preferred. However, the frequency of the application may be varied according to the known systemic absorption of cumulative dosages of the progestational compound in the compositions such that the cumulative dosage over a given period of time will be maintained short of that known to be systemically absorbed. In the case of compositions containing very small doses of the progestational compound, for example, less than 10 micrograms per metered amount of foam, more than one application daily may be given. Accordingly, the dose of progestational compound is determined by the point in the menstrual cycle when treatment is initiated, and by amounts of the specific progestational compound which will be systemically absorbed. Thus, treatment with some progestational compounds may be initiated after the menstrual cycle beings, since certain of such compounds may be administered in larger doses than others for attaining sufficient thickening of mucal secretations but without systemic absorption. For instance, it is possible to apply the self-administrable anti-fertility compositions according to a prescribed regime, wherein the daily or cumulative dosage of the active ingredient is geared to the specific mammal's own production of progesterone during the menstrual cycle and this regime may further be tailored to the individual mammal's own characteristics. That is, the dosage of the progestational compound can be higher during the period of the menstrual cycle when the body's own production of progesterone is low, and lower during the period of menstrual cycle when the body is producing progesterone at a higher rate. The dose applied is effective for alteration of cervical mucus secretions in a manner unfavorable to fertility, resulting from the creation of a barrier of mucus secretions which prevent semen from penetrating to the cervix, such amount also selected according to the progestational compound and dosage quantity and schedule so as to apply to the cervix substantially only a non-systemic quantity of the progestational compound to produce substantially only a local effect without changing in significant measure the amount of said compound in the blood stream of the user and, thereby, without generating side effects resulting from increased blood levels in the user of said compound in the progrestational compound. For the known progestational compounds, however, a daily dose of about 10 micrograms to about 5 milligrams with the onset of menses will be effective to cause a barrier against sperm transport during that cycle.

As with any change over from one contraceptive technique to another, or with the initiation of a contraceptive technique when none was previously used, it is advisable, for absolute maximum safety, to combine the present method with one of the many other available contraceptive methods, such as spermicide foams, condoms, etc., for the first menstrual cycle.

As contrasted with fertility control by use of spermicides, which must be administered about 1 or 2 hours precoitally, the compositions of the invention do not depend upon a relationship in time to coitus, and, therefore, provide more effective fertility control. This time independance for application, according to the present invention, results from the residual effect of previously absorbed (through the cervical epithelium) progestational compound. However, for optimum effectiveness, it is preferred that the daily application, particularly for the period of the menstrual cycle immediately after the last day of the menstrual discharge, be uninterrupted. It is also preferred, for optimum effectiveness, that the daily application be given at the same time each day, whether morning, afternoon, or evening. Such regime is beneficial, both from the point of view of a convenient reminder or scheduling device for the user and to allow the progestational compound to exert its mucus modification function.

At the same time, the compositions of the invention have the additional advantage over conventional spermicidal foams of protecting the cervical tissues, whereas spermicides often injure such tissues or have other harmful side effects.

The practice of douching is not recommended and the composition should be kept in place in the vagina for as long as possible. Moreover, unlike conventional spermicidal foams, it is not required to reapply the antifertility compositions of the present application for each act of coitus in a single day, a single daily non-systemic application being sufficient.

The following examples are intended as further illustration of the invention, but are not necessarily limitative except as set forth in the claims. All parts and percentages are by weight unless otherwise indicated.

EXAMPLE 1

An easily foamable emulsion was prepared with the following ingredients:

| Cationic Foaming Agent | Wt. % |
| --- | --- |
| [1]Triethanolamine lauryl sulfate (40% active) | 25.00 |
| Propylene glycol (U.S.P. XVIII) | 40.00 |
| [2]Progesterone, synthetic | 0.25 |
| Cetyl alcohol (National Formulary XIII) | 3.50 |
| [3]Lauric acid diethanolamide (90% conc.) | 3.20 |
| [4]Perfume, floral | 0.20 |
| [5]Hydroxyethyl cellulose | 0.30 |
| Water (deionized or distilled), to make | 100.00 |

[1]Stephanol WAT - Stepan Chemical Co.
[2]Upjohn Company
[3]Onyx Chemical Co. Super Amide L-9
[4]Perry Bros. Floral K-69-567
[5]Union Carbide Cellosize QP-52,000

The progesterone and cetyl alcohol were dissolved in heated propylene glycol. The cellulose material was dissolved in water to form a stock solution. The remaining ingredients were then admixed and the mixture then added slowly with stirring to the cellulose solution at about 45° C. The resulting emulsion had a pH of 7.0 and was pearly white when cooled to room temperature. The cellulose material helped to keep the cetyl alcohol emulsified.

A sample of the foregoing composition, 85g., was sealed into an aerosol container equipped with a release valve and Freon 114 propellant, 15g., was injected into the container through the valve. The propellant sank to the bottom of the container but was emulsified with the mixture in the container when the container was carefully shaken. The foam which formed and which was extruded when the value as actuated was stable for over an hour and did not flow. While 40% propylene glycol gave the most stable foam, good foam stability was also achieved using 20% and 30% propylene glycol, and 18% butylene glycol. Foam stability lessened substantially when the cetyl alcohol was omitted. The above formula without propellant was also effectively foamed by withdrawing 18 ml and 7.5 ml samples from an open vessel with commercially available syringes or by withdrawing samples by means of a tube connected to a piston.

By any of such foaming and dispensing means, the foamed product can easily be injected into the vaginal cavity.

EXAMPLE 2

| Non-ionic Foaming Agents | Wt. % |
| --- | --- |
| Sorbitan monolaurate | 10.0 |
| Propylene glycol | 40.0 |
| Progesterone, synthetic | 0.25 |
| Cetyl alcohol | 3.5 |
| Lauric acid diethanolamide | 2.5 |
| Hydroxyethyl cellulose | 0.3 |
| Water, to make | 100.0 |

The composition is prepared substantially as described in Example 1 and has substantially equivalent properties.

EXAMPLE 3

| Cationic Foaming Agent | Wt. % |
| --- | --- |
| N-(lauroyl colamino formyl methyl) pyridinium chloride | 10.0 |
| Polyethylene glycol 400 | 35.0 |
| Progesterone, synthetic | 0.25 |
| Lauric acid diethanolamide (acid free) | 2.0 |
| Myristyl alcohol | 4.0 |
| Hydroxyethyl cellulose | 0.3 |
| Water, to make | 100.0 |

The composition is prepared substantially as described in Example 1 and has substantially equivalent properties.

EXAMPLE 4

| Amphoteric Foaming Agent | Wt. % |
| --- | --- |
| [1]Miranol CS | 25.0 |
| Glycerine | 20.0 |
| Progesterone, synthetic | 0.25 |
| Lauric acid diethanolamide | 4.0 |
| Stearyl alcohol | 3.0 |
| Hydroxyethyl cellulose | 0.5 |
| Water, to make | 100.0 |

[1]Sulfonated fatty acid imidazolinium condensate, Miranol Chemical Co.

The composition is prepared substantially as described in Example 1 and has substantially equivalent properties.

EXAMPLE 5

| Anionic Foaming Agent | Wt. % |
| --- | --- |
| Sodium lauryl ether sulfate (25% active) | 30.0 |
| 1,3-Butylene glycol | 30.0 |
| Progesterone, synthetic | 0.25 |
| Behenic alcohol | 2.0 |
| Oleic acid diethanolamide | 3.0 |
| Carboxymethyl cellulose | 0.4 |
| Water, to make | 100.0 |

The composition is prepared substantially as described in Example 1 and has substantially equivalent properties.

EXAMPLE 6

Seven postmenopausal women served as subjects. Nightly they placed one applicator of foam in their vagina. The foam was supplied by the EMKO Company and consisted of the carrier materials used in their "dienestrol vaginal foam" (however, without the dienestrol). Foam was either "control" without progesterone or contained progesterone formulated to provide either 2 or 5 mg per vaginal application. Each subject participated in the study for two weeks. During the first week she inserted one applicator of control foam (without any progesterone) into her vagina each evening. On days 6 and 7 of this control period, each subject collected a 24 hour urine and had a blood sample removed from her antecubital vein. During the next week, three subjects inserted foam containing 2 mg per applicator in their vagina each evening, whereas 4 subjects inserted 5 mg per applicator. Again, on the last two days of this interval, 24 hour urines were collected and blood was drawn. Each 24 hour urine was analyzed for pregnanediol. Each plasma sample was analyzed for progesterone. Pregnanediol determinations were performed by Bio-Science Laboratory of Van Nuys, Calif. Progesterone was determined according to the method of Abraham using radioimmunossay techniques.

Statistical analysis of the data compared mean controlled and mean treatment values using a t-test for paired comparisons. The results are shown in the following table:

| | MEAN VALUES | | | |
|---|---|---|---|---|
| | Control | 2 mg dose | Control | 5 mg dose |
| Pregnanediol mg/24 hrs | 0.6 | 0.6 | 0.6 | 0.9 |
| Progesterone ng/ml | 0.2 | 0.4 | 0.4 | 0.8 |

No difference significant at p = 0.01

Any increase in serum progesterone resulting from administration of 5 mg of progesterone per vagina nightly×7 days does not appear to be of physiologic significance. This is illustrated by examination of follicular and luteal phase serum progesterone levels. The mean ±1 standard deviation for follicular phase serum progesterone concentrations is 0.47±0.1. Similar figures for the luteal phase are 7.7±4.3. Thus, the increased serum concentration of progesterone noted following administration of 5 mg of progesterone per vagina merely brings the serum concentration to that normally present during the follicular phase. During the follicular phase of the normal ovulatory cycle, progesterone is not thought to exert any significant biological effect and certainly does not act in any way as a contraceptive. Thus, the observed increase in serum progesterone does not result in a biologically significant increase and any contraceptive effects of the vaginally administered progesterone could not be ascribed to the systemic effects of the absorbed progesterone. That is, there is no significant likelihood of systemic effects resulting from the daily application, to the vagina, of 5 mg progesterone.

Therefore, the levels of progesterone resulting from 5 mg vaginal application are levels which clearly have no effect on "biological function or condition of the user other than the vagina, cervix or uterus" and "the blood level of the progestational compound is " not "significantly in excess of what it is naturally."

In view of the foregoing description, it will be apparent that the invention is not limited to the specific details set forth therein for the purposes of illustration, and that various other modifications are equivalent for the stated and illustrated functions without departing from the spirit and scope of the invention.

What is claimed is:

1. A self-administrable antifertility composition comprising a progestational compound for topical non-systemic application to the cervix in an amount effective for alteration of cervical mucous secretions in a manner unfavorable to fertility and a non-rigid pharmaceutically acceptable viscous gel, cream, foam or effervescent type suppository vehicle which is sufficiently viscous to keep the progestational compound in effective contact with the cervical tissue for sufficient time to bring about the desired modification of the cervical mucous secretions when formulated for self-administrable use, care being taken that the carrier is not so viscous that administration becomes difficult and the contact time required between the reactive progestational ingredient and the cervical tissue becomes overly long for the effective dose to be administered, said vehicle excluding solid or rigid type ampoules or capsules as well as liquid carriers and ordinary suppositories which have an undesirable propensity to flow and run out of the vagina, said progestational compound being contained in said vehicle in a concentration selected according to the progestational compound and the dosage quantity and schedule so as to apply to the cervix substantially only a non-systemic quantity of the progestational compound to produce substantially only a local effect without changing in significant measure the amount of said compound in the blood stream of the user and thereby without generating side effects resulting from increased blood levels in the user of said progestational compound.

2. A composition as in claim 1 wherein said vehicle comprises a foam base containing a thickening agent in an amount effective to substantially prevent said composition from flowing when foamed.

3. A composition as in claim 1 further comprising a foam containing a stabilizing agent.

4. A composition as in claim 2 wherein said thickening agent is an aliphatic, straight chain, monohydroxy alcohol containing 14-22 carbon atoms.

5. A composition as in claim 1 wherein said composition is an aqueous emulsion, said emulsion containing about 1-5% by weight of a thickening agent comprising an aliphatic, straight chain monohydroxy alcohol containing 14-22 carbon atoms, and an anionic surfactant as a foaming agent in an amount of about 5-20% by weight.

6. A composition as in claim 5 further including a fatty acid-dialkanolamine condensate in an amount of about 1-5% by weight.

7. A composition as in claim 1 further comprising a foam containing a stabilizing agent.

8. A composition as in claim 7 wherein said foam stabilizing agent is a glycol, a polyalkylene glycol or glycerol, present in said composition in an amount of about 10-50% by weight.

9. A composition as in claim 6 further including a foam stabilizing agent selected from a glycol, a polyalkylene glycol and glycerol, said foam stabilizing agent being present in an amount of about 10-50% by weight.

10. A composition as in claim 1 wherein the amount of progestational compound is insufficient to provide a dose of greater than about 5 milligrams per application.

11. A composition as in claim 1 wherein the amount of said progestational compound is sufficient to provide a dose of from about 10 micrograms to about 5 milligrams.

12. A composition as in claim 1 wherein said composition is an aqueous emulsion, said composition containing triethanolamine lauryl sulfate as a foaming agent and said progestational compound is progesterone, said composition further containing about 10-50% of propylene glycol or ethylene glycol, about 1-5% by weight of coconut-diethanolamine condensate, about 1-5% by weight of cetyl alcohol, about 0.1-2% by weight of hydroxyethyl cellulose or hydroxypropyl cellulose, and about 20–50% by weight of water.

13. A composition as in claim 1 wherein said composition containing as a foaming agent a surfactant selected from triethanolamine lauryl sulfate, sorbitain monolaurate, N-(lauroyl colamino formyl methyl) pyridinium chloride, a carboxylic acid derivative of an imidazolinium compound, and sodium lauryl ether sulfate, the amount of said surfactant being about 5–20%, and wherein the progestational compound is progesterone, said composition further containing about 10–50% by weight of ethylene glycol, propylene glycol, a polyalkylene glycol or glycerol, about 1–5% by weight of coconut-diethanolamine condensate or oleic acid-diethanolamine condensate, about 1–5% by weight of cetyl alcohol, myristyl alcohol or stearyl alcohol, about 0.1–2% by weight of hydroxyethyl cellulose, hydroxypropyl cellulose, carboxymethyl cellulose, or methyl cellulose, and about 20–50% by weight of water.

14. A composition as in claim 1 wherein the amount of said progestational compound is about 1.25% by weight.

15. A composition as in claim 1 wherein said progestational compound is progesterone.

16. A composition as in claim 1 wherein said progestational compound is natural progesterone, synthetic progesterone, chloromadinone, medroxyprogesterone acetate, norgestrel, or cyproterone acetate.

* * * * *